United States Patent
Eguchi et al.

(10) Patent No.: US 10,488,329 B2
(45) Date of Patent: Nov. 26, 2019

(54) CALIBRATION APPARATUS, CALIBRATION CURVE CREATION METHOD, AND INDEPENDENT COMPONENT ANALYSIS METHOD

(71) Applicant: Seiko Epson Corporation, Tokyo (JP)

(72) Inventors: Tsukasa Eguchi, Matsumoto (JP); Hideto Ishiguro, Shiojiri (JP); Hikaru Kurasawa, Shiojiri (JP)

(73) Assignee: Seiko Epson Corporation (JP)

( * ) Notice: Subject to any disclaimer, the term of this patent is extended or adjusted under 35 U.S.C. 154(b) by 157 days.

(21) Appl. No.: 15/708,610

(22) Filed: Sep. 19, 2017

(65) Prior Publication Data

US 2018/0088034 A1    Mar. 29, 2018

(30) Foreign Application Priority Data

Sep. 26, 2016    (JP) .................................. 2016-186729

(51) Int. Cl.
  *G01N 21/27*    (2006.01)
  *G01N 21/359*   (2014.01)

(52) U.S. Cl.
  CPC ......... *G01N 21/274* (2013.01); *G01N 21/359* (2013.01); *G01N 2201/12746* (2013.01)

(58) Field of Classification Search
  CPC .... G01N 21/274; G01N 21/359; G01N 21/35; G01N 2201/1293; G01N 2201/12746
  See application file for complete search history.

(56) References Cited

U.S. PATENT DOCUMENTS

| 9,921,201 B2* | 3/2018 | Arai ................... G01N 33/0098 |
| 2013/0197816 A1* | 8/2013 | Kurasawa ............ G01N 21/274 |
| | | 702/27 |
| 2016/0091417 A1 | 3/2016 | Kurasawa et al. |
| 2016/0103063 A1* | 4/2016 | Kurasawa ............ G01N 21/359 |
| | | 250/252.1 |

FOREIGN PATENT DOCUMENTS

| JP | 2006-271815 A | 10/2006 |
| JP | 2013-036973 A | 2/2013 |
| JP | 2013-160574 A | 8/2013 |
| JP | 2016-065803 A | 4/2016 |

OTHER PUBLICATIONS

K. Uetsuki et al., "Prediction of Facial Color Variation by Using Independent Component Analysis and Evaluation on Facial Images", Journal of the Society of Photographic Science and Technology of Japan, vol. 64, No. 4, pp. 255-263 (2001).

* cited by examiner

*Primary Examiner* — Bryan Bui
(74) *Attorney, Agent, or Firm* — Harness, Dickey & Pierce, P.L.C.

(57) ABSTRACT

A calibration data acquisition unit uses an equation X=YW in which an optical spectrum matrix X is the same as a product between a component natural spectrum matrix Y and a component amount matrix X, performs independent component analysis in which column vectors of the component amount matrix W are treated as independent components so as to determine the component natural spectrum matrix Y, and employs row vectors of a general inverse matrix $Y^\dagger$ of the component natural spectrum matrix Y as component calibration spectra corresponding to a plurality of components. A calibration curve is created by using a target component calibration spectrum corresponding to a target component.

3 Claims, 7 Drawing Sheets

CALIBRATION APPARATUS, CALIBRATION CURVE CREATION METHOD, AND INDEPENDENT COMPONENT ANALYSIS METHOD

BACKGROUND

1. Technical Field

The present invention relates to a calibration technique of obtaining a component amount of a target component from measured data of a test object, and an independent component analysis technique of determining an independent component on the basis of measured data such as an optical spectrum.

2. Related Art

In the related art, there is a calibration method of obtaining a component amount of a target component by using independent component analysis (ICA). The independent component analysis of the related art is a method of estimating signal sources as independent components on the premise that the signal sources (for example, an optical spectra) derived from a plurality of components are independent components. For example, JP-A-2013-36973 discloses a calibration technique in which an optical spectrum is acquired by performing spectrometry on a green vegetable, a spectrum derived from chlorophyll is estimated as an independent component by performing independent component analysis on the optical spectrum, and a chlorophyll amount in a new green vegetable sample is determined by using the estimated spectrum.

Meanwhile, in order to sufficiently accurately perform independent component analysis, the condition that a plurality of independent components to be estimated are statistically independent from each other is required to be established. However, in a certain kind of measured data, such a condition for performing accurate independent component analysis may not be established.

In this case, there is a probability that optical spectra cannot be accurately estimated even if normal independent component analysis in which optical spectra derived from a plurality of components are treated as independent components is performed. Therefore, a technique of performing independent component analysis with high accuracy or a technique of calibrating a target component with high accuracy is desirable even in a case where the condition that optical spectra derived from a plurality of components are "statistically independent from each other" is not satisfied. This problem is not limited to calibration of a target component using an optical spectrum including a near-infrared region, and is common to other techniques of performing independent component analysis on other measured data or measured signals.

SUMMARY

An advantage of some aspects of the invention is to solve at least a part of the problems described above, and the invention can be implemented as the following forms or application examples.

(1) According to a first aspect of the invention, a calibration apparatus obtaining a component amount for a target component in a test object is provided. The calibration apparatus includes an optical spectrum acquisition unit that acquires an optical spectrum obtained through spectrometry on the test object; a calibration data acquisition unit that acquires calibration data including a target component calibration spectrum corresponding to the target component, and a single regression formula indicating a calibration curve; an inner product value calculation unit that computes an inner product value between the optical spectrum measured for the test object and the target component calibration spectrum; and a component amount calculation unit that calculates a component amount for the target component corresponding to an inner product value obtained by the inner product value calculation unit by using the single regression formula indicating a relationship between the inner product value and a component amount for the target component. wherein the calibration data acquisition unit performs (a) a process of acquiring M optical spectra obtained through spectrometry on M (where M is an integer of 2 or more) first samples each containing N (where N is an integer of 1 or more) components including the target component, S evaluation spectra obtained through spectrometry on S (where S is an integer of 3 or more) second samples in which a component amount for the target component is known; (b) a process of using an equation X=YW in which an optical spectrum matrix X having optical spectra obtained through spectrometry on each of the M first samples as column vectors is the same as a product between a component natural spectrum matrix Y having unknown component natural spectra derived from the N respective components as column vectors and a component amount matrix W having unknown component amounts for the N components in each of the samples as column vectors, and performs independent component analysis in which the respective column vectors forming the component amount matrix W are treated as independent components, so as to determine the component amount matrix W and the component natural spectrum matrix Y, and also employs N row vectors of a general inverse matrix $Y^\dagger$ of the determined component natural spectrum matrix Y, as the N component calibration spectra corresponding to the N components; (c) a process of performing calculation using a function having each component calibration spectrum or a component natural spectrum corresponding to the component calibration spectrum as a variable with respect to each of the N component calibration spectra, so as to calculate an evaluation value of each component calibration spectrum; (d) a process of selecting a component calibration spectrum causing the evaluation value to be greatest as the target component calibration spectrum among the N component calibration spectra; and (e) a process of creating, as the calibration curve, a single regression formula indicating a relationship between an inner product value obtained through an inner product between the S evaluation spectra and the target component calibration spectrum, and a component amount for the target component contained in the S second samples. According to the calibration apparatus, since independent component analysis in which component amounts for a plurality of components in each sample are treated as independent components is performed, the independent component analysis can be performed with high accuracy, and thus calibration of a target component can be performed with high accuracy, even in a case where optical spectra derived from a plurality of components are not independent from each other.

(2) According to a second aspect of the invention, a calibration curve creation method performed by the calibration data acquisition unit in the first aspect is provided.

According to the calibration method, in the same manner as in the first aspect, it is possible to perform independent component analysis with high accuracy, and to perform calibration of a target component with high accuracy.

(3) According to a third aspect of the invention, an independent component analysis method in which component calibration spectra corresponding to a plurality of components contained in each sample are determined on the basis of a plurality of optical spectra obtained through spectrometry on a plurality of samples is provided. The independent component analysis method includes (1) using an equation X=YW in which an optical spectrum matrix X having optical spectra obtained through spectrometry on each of the plurality of samples as column vectors is the same as a product between a component natural spectrum matrix Y having unknown component natural spectra derived from the plurality of respective components as column vectors and a component amount matrix W having unknown component amounts for the plurality of components in each of the samples as column vectors, and performs independent component analysis in which the respective column vectors forming the component amount matrix W are treated as independent components, so as to determine the component amount matrix W and the component natural spectrum matrix Y; and (2) employing respective row vectors of a general inverse matrix $Y^\dagger$ of the component natural spectrum matrix Y determined through the independent component analysis, as a plurality of component calibration spectra corresponding to the plurality of components. According to this method, since independent component analysis in which component amounts for a plurality of components in each sample are treated as independent components is performed, the independent component analysis can be performed with high accuracy, even in a case where optical spectra derived from a plurality of components are not independent from each other.

The invention may be realized in aspects such as an electronic apparatus including the above-described apparatus, a computer program for realizing functions of the respective units of the apparatus, and a non-transitory storage medium which stores the computer program thereon.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an embodiment of the invention will be described in the following order.

A. Overview of independent component analysis in which component amounts are treated as independent components B. Overview of calibration curve creation process and calibration process C. Configuration of calibration apparatus and process content thereof in embodiment D. Content of calibration data acquisition process E. Modification examples A. OVERVIEW OF INDEPENDENT COMPONENT ANALYSIS IN WHICH COMPONENT AMOUNTS ARE TREATED AS INDEPENDENT COMPONENTS Independent component analysis used in an embodiment described below is greatly different from typical independent component analysis in which component-derived measured data (for example, an optical spectrum) is treated as an independent component in that a component amount for a component is treated as an independent component. Therefore, first, a description will be made of a difference between the typical independent component analysis and the independent component analysis in which a component amount is treated as an independent component. Hereinafter, for convenience of description, a description will be made of a case of using an optical spectrum of a test object (also referred to as a "sample") as measured data, but the independent component analysis in which a component amount is treated as an independent component is applicable to different kinds of signals or data such as a sound signal or an image.

In the typical independent component analysis, for example, optical spectra $x_1(\lambda)$, $x_2(\lambda)$, and $x_3(\lambda)$ obtained through spectrometry on a plurality of samples are expressed as in the following Equation (1) as a linear combination of component natural spectra $s_1(\lambda)$, $s_2(\lambda)$, and $s_3(\lambda)$ derived from a plurality of components contained in each sample.

$$\left.\begin{array}{l} x_1(\lambda) = a_{11}s_1(\lambda) + a_{12}s_2(\lambda) + a_{13}s_3(\lambda) \\ x_2(\lambda) = a_{21}s_1(\lambda) + a_{22}s_2(\lambda) + a_{23}s_3(\lambda) \\ x_3(\lambda) = a_{31}s_1(\lambda) + a_{32}s_2(\lambda) + a_{33}s_3(\lambda) \end{array}\right\} \quad (1)$$

Here, $a_{11}$, $a_{12}$, . . . , and $a_{33}$ are weighting factors indicating component amounts for the respective components. Herein, for convenience of description, the number of samples and the number of components in optical spectra are assumed to be all three.

The above Equation (1) is expressed as in the following Equation (2) in terms of a matrix.

$$\begin{bmatrix} x_1(\lambda) \\ x_2(\lambda) \\ x_3(\lambda) \end{bmatrix} = A \begin{bmatrix} s_1(\lambda) \\ s_2(\lambda) \\ s_3(\lambda) \end{bmatrix} \quad (2)$$

$$A = \begin{bmatrix} a_{11} & a_{12} & a_{13} \\ a_{21} & a_{22} & a_{23} \\ a_{31} & a_{32} & a_{33} \end{bmatrix}$$

In the typical independent component analysis, unknown component natural spectra $s_1(\lambda)$, $s_2(\lambda)$, and $s_3(\lambda)$ derived from a plurality of components are treated as components which are independent from each other, and are subjected to independent component analysis by using the above Equation (2). In this case, in order to sufficiently accurately perform independent component analysis, the condition that a plurality of component natural spectra $s_1(\lambda)$, $s_2(\lambda)$, and $s_3(\lambda)$ are statistically independent from each other is required to be established.

However, the condition for performing accurate independent component analysis may not be established depending on property of measured data. In this case, optical spectra derived from a plurality of components may not satisfy the condition of being "statistically independent from each other". In this case, even if the typical independent component analysis is performed by using the above Equation (2), the component natural spectra $s_1(\lambda)$, $s_2(\lambda)$, and $s_3(\lambda)$ or the component amount matrix A cannot be accurately estimated.

The present inventor of the invention has found that the component natural spectra $s_1(\lambda)$, $s_2(\lambda)$, and $s_3(\lambda)$ or the component amount matrix A can be accurately estimated or determined by employing the independent component analysis in which a component amount is treated as an independent component instead of the above-described typical independent component analysis.

In the independent component analysis in which a component amount is treated as an independent component, the following equation is used instead of the above Equation (2).

$$[x_1(\lambda)^T \; x_2(\lambda)^T \; x_3(\lambda)^T] = [s_1(\lambda)^T \; s_2(\lambda)^T \; s_3(\lambda)^T] A^T \qquad (3)$$

$$A^T = \begin{bmatrix} a_{11} & a_{12} & a_{13} \\ a_{21} & a_{22} & a_{23} \\ a_{31} & a_{32} & a_{33} \end{bmatrix}$$

Here, the superscript "T" added to the matrix symbol indicates a transposed matrix. Equation (3) is obtained by transposing both of the sides in the above Equation (2).

In the independent component analysis in which a component amount is treated as an independent component, in the above Equation (3), the column vectors $[a_{11} \; a_{12} \; a_{13}]^T$, $[a_{21} \; a_{22} \; a_{23}]^T$, and $[a_{31} \; a_{32} \; a_{33}]^T$ of the component amount matrix $A^T$ are respectively treated as independent components, and independent component analysis is performed. These column vectors indicate component amounts for a plurality of components in each sample.

The independent component analysis in which a component amount is treated as an independent component is an analysis method employed through the following examination. As described above, there is a case where component natural spectra derived from a plurality of components do not satisfy the condition of being statistically independent from each other. However, although component natural spectra derived from a plurality of components are not statistically independent from each other, if the condition that component amounts (for example, concentrations) for the plurality of components have no relation to each other and are statistically independent from each other is established, in a case where component amounts (that is, the respective column vectors forming the component amount matrix $A^T$ in the above Equation (3)) for a plurality of components in each sample are treated as independent components, and independent component analysis is performed, it is possible to accurately estimate or determine the component amount matrix $A^T$, and also to accurately estimate or determine the component natural spectra $s_1(\lambda)$, $s_2(\lambda)$, and $s_3(\lambda)$.

If the above Equation (3) is generalized, the following Equation (4) is obtained.

$$X^T = S^T A^T \qquad (4)$$

$$X^T = \begin{bmatrix} x_1(\lambda_1) & \cdots & x_M(\lambda_1) \\ \vdots & \ddots & \vdots \\ x_1(\lambda_K) & \cdots & x_M(\lambda_K) \end{bmatrix}$$

$$S^T = \begin{bmatrix} s_1(\lambda_1) & \cdots & s_N(\lambda_1) \\ \vdots & \ddots & \vdots \\ s_1(\lambda_K) & \cdots & s_N(\lambda_K) \end{bmatrix}$$

$$A^T = \begin{bmatrix} a_{11} & \cdots & a_{M1} \\ \vdots & \ddots & \vdots \\ a_{1N} & \cdots & a_{MN} \end{bmatrix}$$

Here, K indicates the number of measurement points of the wavelength $\lambda$ in a spectrum, M indicates the number of samples, and N indicates the number of components. A component amount $a_{mn}$ (where m is 1 to M, and n is 1 to N) is a component amount (for example, a concentration) for an n-th component in an m-th sample.

Since it is inconvenient to use matrices $X^T$, $S^T$, and $A^T$ as in the above Equation (4) with the transposition symbol, $X = X^T$, $Y = S^T$, $y_n(\lambda_k) = s_n(\lambda_k)$, $W = A^T$, and $w_{mn} = a_{mn}$ are set, and the above Equation (4) is rewritten into the following Equation (5) which is used in independent component analysis in which a component amount is treated as an independent component.

Equations used in independent component analysis in which component amount is treated as independent component $$X = YW \qquad (5)$$

$$X = \begin{bmatrix} x_1(\lambda_1) & \cdots & x_M(\lambda_1) \\ \vdots & \ddots & \vdots \\ x_1(\lambda_K) & \cdots & x_M(\lambda_K) \end{bmatrix}$$

$$Y = \begin{bmatrix} y_1(\lambda_1) & \cdots & y_N(\lambda_1) \\ \vdots & \ddots & \vdots \\ y_1(\lambda_K) & \cdots & y_N(\lambda_K) \end{bmatrix}$$

$$W = \begin{bmatrix} w_{11} & \cdots & w_{M1} \\ \vdots & \ddots & \vdots \\ w_{1N} & \cdots & w_{MN} \end{bmatrix}$$

Here, $x_m(\lambda_k)$ indicates a spectral intensity at a wavelength $\lambda_k$ in an m-th sample, $y_n(\lambda_k)$ indicates a spectral intensity at the wavelength $\lambda_k$ derived from an n-th component, and $w_{mn}$ indicates a component amount for the n-th component in the m-th sample. K indicates the number of measurement points of the wavelength $\lambda$ in a spectrum, M indicates the number of samples, and N indicates the number of components. K and M are all integers of 2 or more. N is an integer of 1 or more, and may be an integer of 2 or more.

The above Equation (5) corresponds to an equation in which an optical spectrum matrix X having optical spectra obtained through spectrometry on each sample as column vectors $[x_m(\lambda_1) \; \cdots \; x_m(\lambda_K)]^T$ is the same as a product between a component natural spectrum matrix Y having unknown component natural spectra derived from a plurality of respective components as column vectors $[y_n(\lambda_1) \; \cdots \; y_n(\lambda_K)]^T$ and a component amount matrix W having unknown component amounts indicating component amounts for a plurality of components in each sample as column vectors $[w_{m1} \; \cdots \; w_{mN}]^T$.

Figure 1:
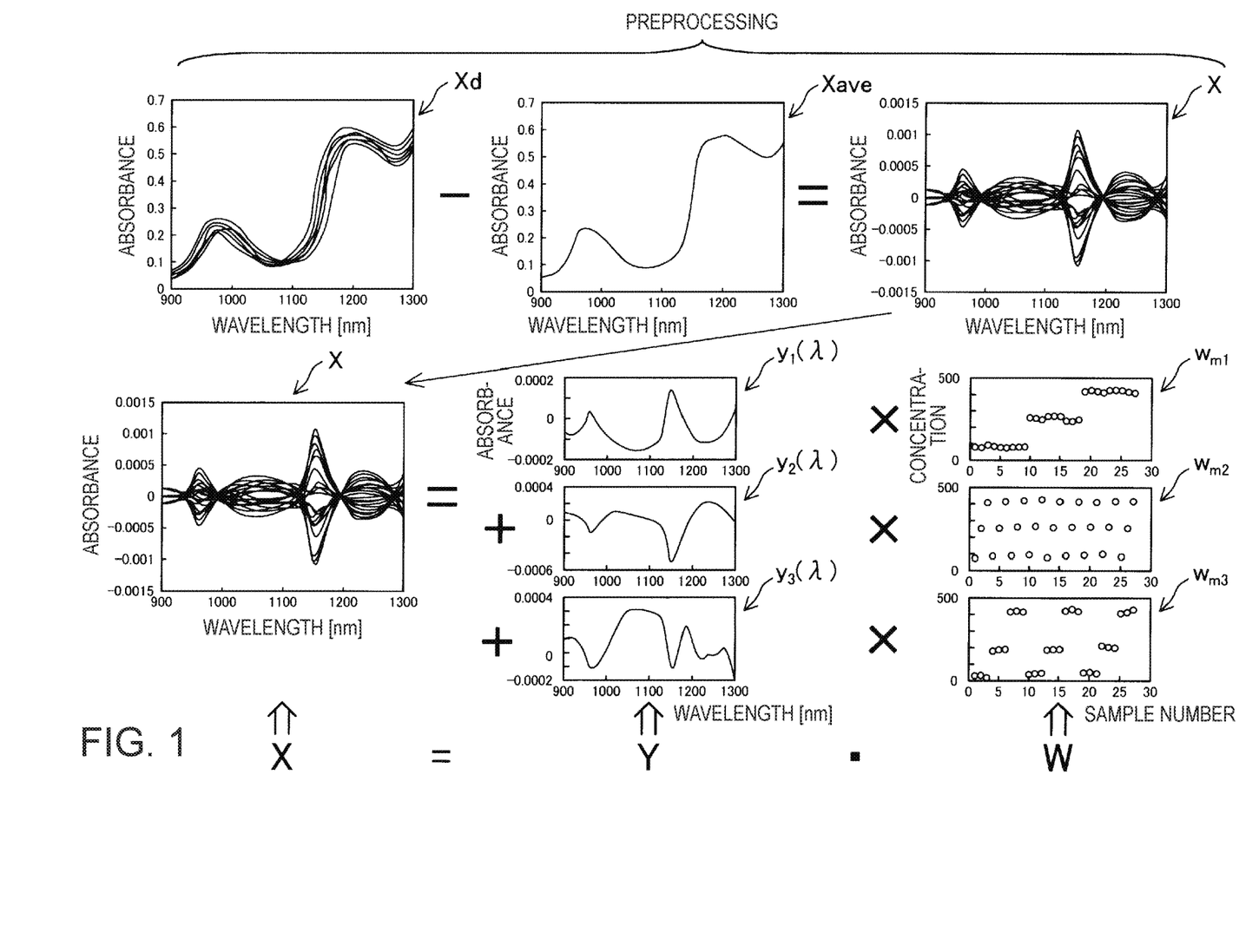
FIG. 1 is a diagram illustrating an overview of independent component analysis in which component amounts are treated as independent components.

FIG. 1 is a diagram illustrating an overview of independent component analysis in which a component amount is treated as an independent component. FIG. 1 illustrates an example of a case where an aqueous solution containing glucose or albumin is used as a sample, and optical spectra obtained through spectrometry on a plurality of samples are used as independent component analysis objects. A measured spectrum Xd is an absorbance spectrum obtained through spectrometry. A plurality of actual measured spectra Xd show considerably approximate curves, but, in FIG. 1, for convenience of illustration, differences among the plurality of measured spectra Xd are illustrated to be exaggerated. The measured spectra Xd for a plurality of samples have values approximate to each other, and, thus, if these values are used as they are, there is a probability that the accuracy of a result obtained through independent component analysis may not be sufficiently high. For example, the influence of a solvent on a measured spectrum may change depending on the concentration of a solute (contained component), and thus the accuracy of independent component analysis may deteriorate. Therefore, as preprocessing, a subtraction calculation is performed so that an average spectrum Xave of a plurality of measured spectra Xd is subtracted from each measured spectrum Xd, and thus a difference spectrum X is obtained. In the above-described way, even in a case where the influence of a solvent on a measured spectrum changes depending on the concentration of a solute (contained component), the influence can be removed through the preprocessing, and thus it is possible to increase the accuracy of independent component analysis. The difference spectrum X is used as the optical spectrum X in the above Equation (5). If independent component analysis is performed on the difference spectrum X, the accuracy of the independent component analysis can be improved. However, preprocessing may be omitted.

The lower part in FIG. 1 illustrates a state in which the optical spectrum X is expressed by a product between the unknown component natural spectrum $y_n(\lambda)$ and the unknown component amount $w_{mn}$.

In the independent component analysis, the component amount matrix W is determined by treating each column vector $[w_{m1} \ldots w_{mN}]^T$ of the component amount matrix W as an independent component and performing the independent component analysis, and, as a result, the component natural spectrum matrix Y is also determined. An independent component analysis method may employ the typical independent component analysis. For example, an independent component analysis method disclosed in JP-A-2013-160574 or JP-A-2016-65803 filed by the applicant of the present application may be used, or other independent component analysis methods may be used.

If the component natural spectrum matrix Y in the above Equation (5) is determined, a component amount w* for a plurality of components in a new sample may be obtained by integrating an optical spectrum x* obtained through spectrometry on the new sample with a general inverse matrix $Y^\dagger$ of the component natural spectrum matrix Y obtained through the independent component analysis. Specifically, the component amount w* for the components of the new sample may be obtained by using the following Equation (6).

$$w^* = Y^\dagger x^* \qquad (6)$$

$$w^* = \begin{bmatrix} w_1^* \\ \vdots \\ w_N^* \end{bmatrix}$$

$$Y = \begin{bmatrix} y_1^\ddagger(\lambda_1) & \cdots & y_1^\ddagger(\lambda_K) \\ \vdots & \ddots & \vdots \\ y_N^\ddagger(\lambda_K) & \cdots & y_N^\ddagger(\lambda_K) \end{bmatrix}$$

$$W = \begin{bmatrix} x^*(\lambda_1) \\ \vdots \\ x^*(\lambda_K) \end{bmatrix}$$

Here, $w^* = [w_1^* \ldots w_N^*]^T$ is a component amount for N components included in a new sample, $Y^\dagger$ is a general inverse matrix of the component natural spectrum matrix Y obtained through independent component analysis, $y_n(\lambda_k)^\ddagger$ is a k-th element of a row vector of an n-th row in the general inverse matrix $Y^\dagger$, and $x^* = [x^*(\lambda_1) \ldots x^*(\lambda_K)]^T$ is an optical spectrum obtained through spectrometry on the new sample. The above Equation (6) may be derived by multiplying the lefts of both sides in the above Equation (5) by the general inverse matrix $Y^\dagger$ of the component natural spectrum matrix Y.

A value of a component amount $w_n^*$ for any n-th component of the new sample is obtained according to the following Equation (7) derived from the above Equation (6).

$$w_n^* = y_n^\ddagger x^*$$
$$y_n^\ddagger = [y_n^\ddagger(\lambda_1) \ldots y_n^\ddagger(\lambda_K)] \qquad (7)$$

Here, $y_n^\ddagger$ is a row vector of an n-th row in the general inverse matrix $Y^\dagger$ of the component natural spectrum matrix Y. The row vector $y_n^\ddagger$ is also referred to as an "inverse matrix row vector $y_n^\ddagger$" or a "component calibration spectrum $y_n^\ddagger$". The general inverse matrix $Y^\dagger$ of the component natural spectrum matrix Y is referred to as a "component calibration spectrum matrix $Y^\dagger$". As mentioned above, the general inverse matrix $Y^\dagger$ may be obtained on the basis of the component natural spectrum matrix Y obtained through independent component analysis, and the component amount $w_n^*$ for the n-th component may be obtained by taking an inner product between the inverse matrix row vector $y_n^\ddagger$ (that is, the n-th component calibration spectrum $y_n^\ddagger$) corresponding to the n-th component in the general inverse matrix $Y^\dagger$ and the optical spectrum x* for the new sample. However, the component natural spectrum matrix Y obtained through independent component analysis is meaningless in a value of an element thereof, and has property in which a waveform thereof is proportional to a true component natural spectrum. Therefore, the component amount $w_n^*$ obtained through the inner product in the above Equation (7) is a value which is proportional to an actual component amount. An actual component amount may be obtained by applying the inner product value $w_n^*$ obtained through the inner product in the above Equation (7) to a calibration curve (described later).

As mentioned above, according to the independent component analysis in which a component amount is treated as an independent component, even in a case where component natural spectra derived from a plurality of components are not statistically independent from each other, the component amount matrix W and the component natural spectrum matrix Y (and the component calibration spectrum matrix $Y^\dagger$ which is a general inverse matrix) can be accurately estimated or determined.

B. OVERVIEW OF CALIBRATION CURVE CREATION PROCESS AND CALIBRATION PROCESS

Figure 2:
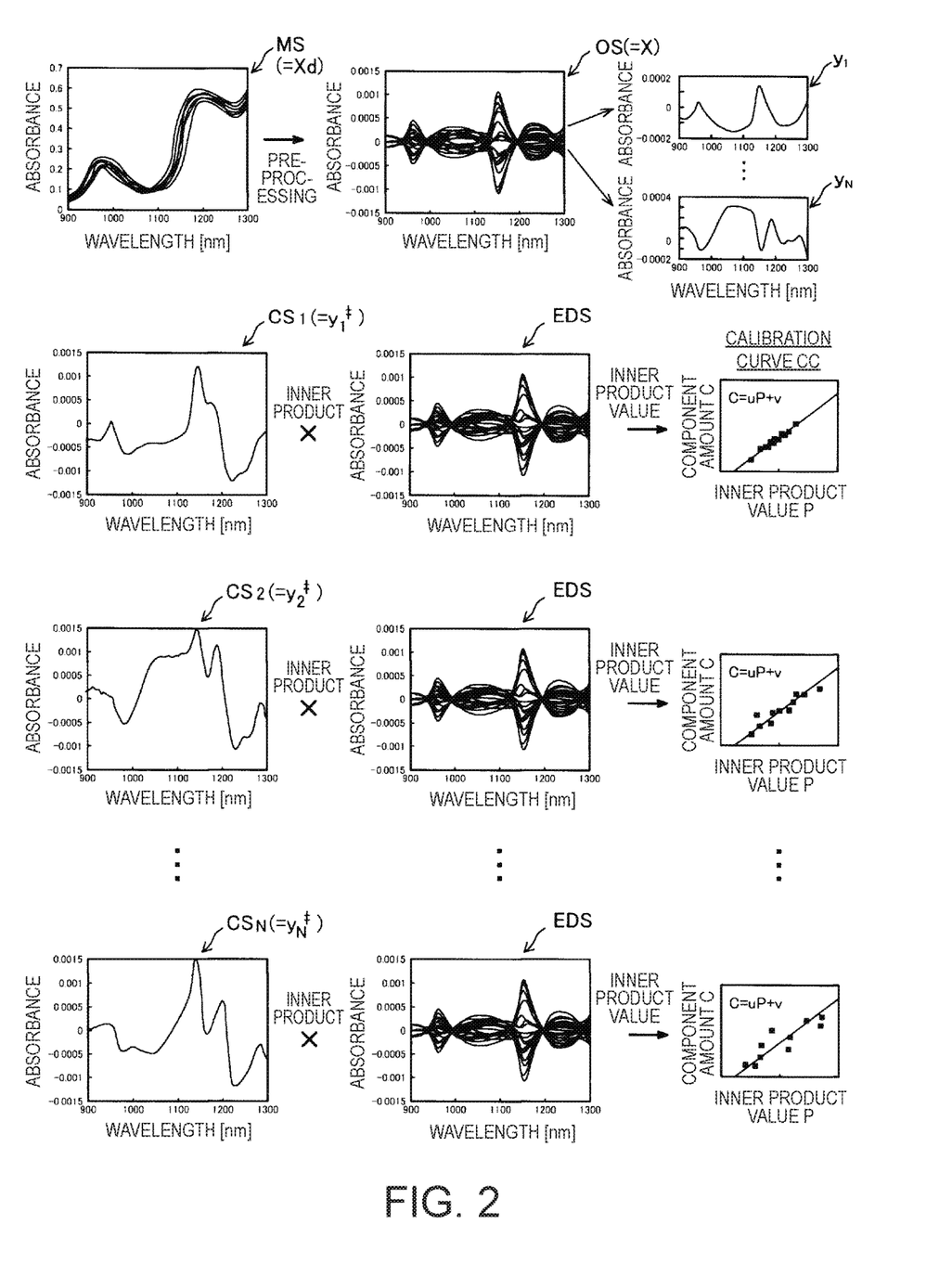
FIG. 2 is a diagram illustrating an overview of a calibration curve creation process using independent component analysis.

FIG. 2 is a diagram illustrating an overview of a calibration curve creation process using independent component analysis (ICA) in which a component amount is treated as an independent component. An upper left part in FIG. 2 illustrates examples of measured spectra MS obtained through spectrometry on a plurality of samples. The measured spectra MS correspond to the measured spectra Xd in FIG. 1, and may be obtained through spectrometry on a sample containing a plurality of components (for example, glucose and albumin). In atypical calibration curve creation process, as a plurality of samples, known samples in which a component amount (for example, a concentration) for a target component (for example, glucose) is known are used. However, in an embodiment which will be described later, there is a difference from the typical calibration curve creation process in that samples (first samples) in which a component amount for a target component is unknown may be used as a plurality of samples for acquiring optical spectra as independent component analysis objects.

In creation of a calibration curve, first, preprocessing is performed on the measured spectra MS, and thus optical spectra OS (the optical spectra X having undergone preprocessing in FIG. 1) having undergone the preprocessing are created. As the preprocessing, for example, preprocessing including normalization of the measured spectra MS is performed. In the preprocessing, a subtraction calculation described in FIG. 1 is also preferably performed in addition to normalization. In the preprocessing, project on null space (PNS) may be performed in order to remove a baseline variation in the measured spectra MS. However, in a case where initial measured spectra MS have characteristics of not requiring preprocessing (for example, in a case where the measured spectra MS do not vary due to normalization), preprocessing may be omitted, and the measured spectra MS may be used as the optical spectra OS without being changed.

Next, independent component analysis in which a component amount is treated as an independent component is performed on a plurality of optical spectra OS, and thus a plurality of component calibration spectra $CS_1$ to $CS_N$ are obtained. The number in the parenthesis indicates a component number. The plurality of component calibration spectra $CS_1$ to $CS_N$ correspond to the above-described component calibration spectra $y_n^\ddagger$.

A lower part in FIG. 2 illustrates a method of creating a calibration curve by using the plurality of component calibration spectra $CS_1$ to $CS_N$ obtained in the above-described way. Herein, first, optical spectra EDS regarding a plurality of known samples (second samples) in which a component amount for a target component is known are acquired. The optical spectra EDS are obtained by performing, as necessary, the above-described preprocessing on measured spectra which are obtained through spectrometry on the known samples. The optical spectra EDS are referred to as "evaluation spectra EDS". Next, an inner product value between the individual evaluation spectra EDS and the component calibration spectrum CS, is computed. The computation of the inner product value is a calculation in which each of the evaluation spectra EDS and the component calibration spectrum $CS_n$ are treated as a single vector, and an inner product between the two vectors is taken, and, as a result, a single inner product value is obtained. Therefore, if inner products between the same component calibration spectrum $CS_n$ and a plurality of evaluation spectra EDS are computed, a plurality of inner product values corresponding to a plurality of known samples are obtained with respect to the same component calibration spectrum $CS_n$. A lower right part in FIG. 2 shows diagrams in which inner product values P regarding a plurality of known samples are taken on a transverse axis, a known amount C for a target component contained in the plurality of known samples is taken on a longitudinal axis, and the values are plotted. If the n-th component calibration spectrum $CS_n$ used for an inner product is a spectrum corresponding to a target component, as in the example illustrated in FIG. 2, the inner product value P and the component amount C for the target component of each known sample have a strong correlation. Therefore, from among the plurality of component calibration spectra $CS_1$ to $CS_N$ obtained through the independent component analysis, the component calibration spectrum $CS_n$ having the strongest correlation (the greatest correlation degree) may be selected as a target component calibration spectrum corresponding to the target component. As an evaluation value for such selection, evaluation values other than the correlation degree may be used. In the example illustrated in FIG. 2, the first component calibration spectrum $CS_1$ is a target component calibration spectrum corresponding to the target component (for example, glucose). A calibration curve CC is represented as a straight line given by a single regression formula C=uP+v for plotting the inner product value P and the component amount C.

Figure 3:
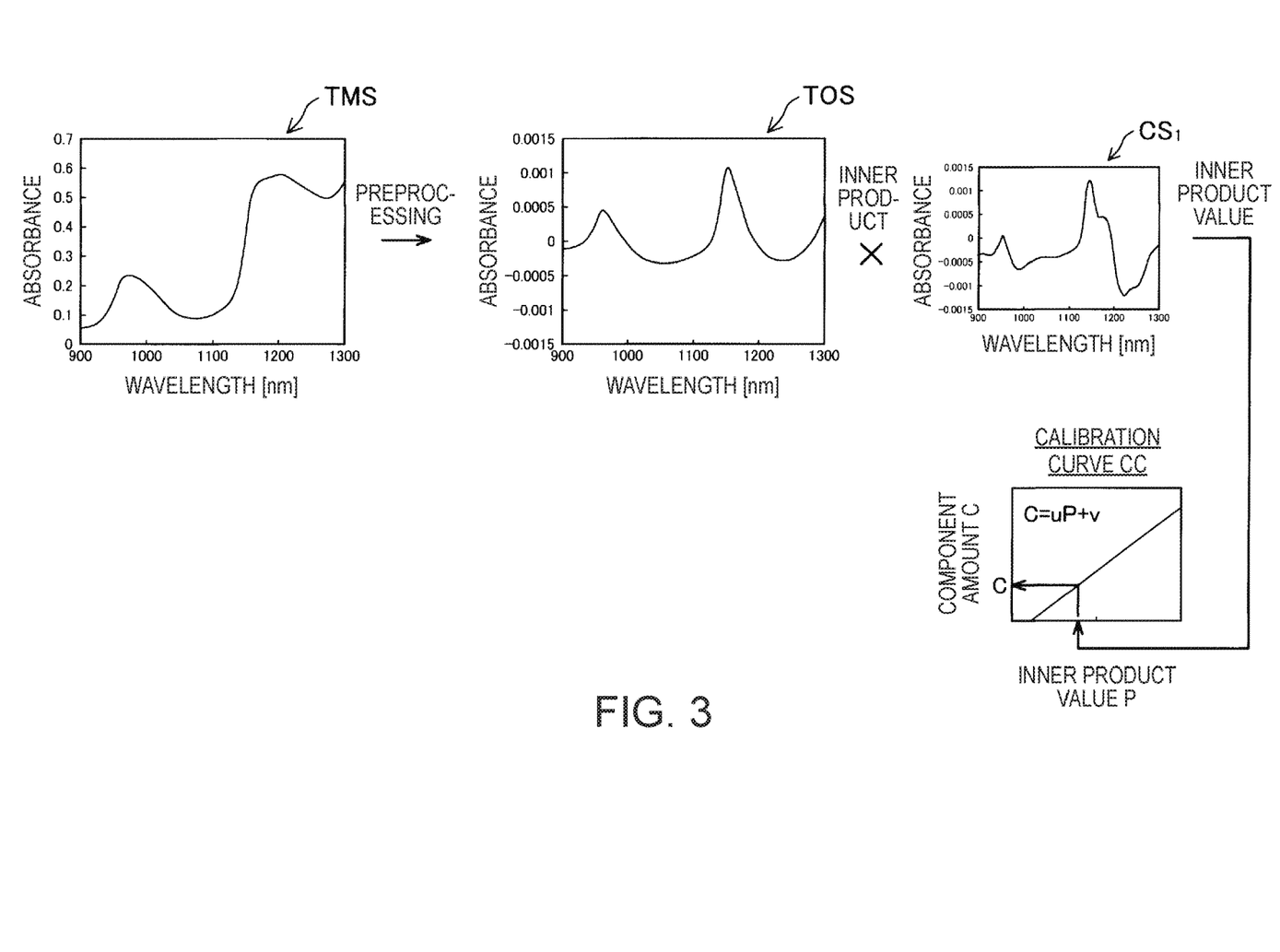
FIG. 3 is a diagram illustrating an overview of a target component calibration process.

FIG. 3 is a diagram illustrating an overview of a target component calibration process using a calibration curve. The calibration process is performed by using the target component calibration spectrum $CS_1$ and the calibration curve CC obtained through the calibration curve creation process illustrated in FIG. 2. In the calibration process, first, a measure spectrum TOS of a test object in which a component amount for a target component is unknown is acquired. Next, preprocessing is performed on the measure spectrum TOS as necessary, and thus an optical spectrum TOS having undergone the preprocessing is created. This preprocessing is the same processing as the preprocessing used for creation of the calibration curve. In the preprocessing during creation of the calibration curve, in a case where a subtraction calculation described in FIG. 1 is performed, the average spectrum Xave used during creation of the calibration curve may be subtracted from the measure spectrum TOS. An inner product between the optical spectrum TOS obtained in the above-described way and the target component calibration spectrum $CS_1$ is taken, and thus an inner product value P regarding the optical spectrum TOS is calculated. If the inner product value P is applied to the calibration curve CC, a component amount C for the target component contained in the test object can be determined.

C. CONFIGURATION OF CALIBRATION APPARATUS AND PROCESS CONTENT THEREOF IN EMBODIMENT

Figure 4:
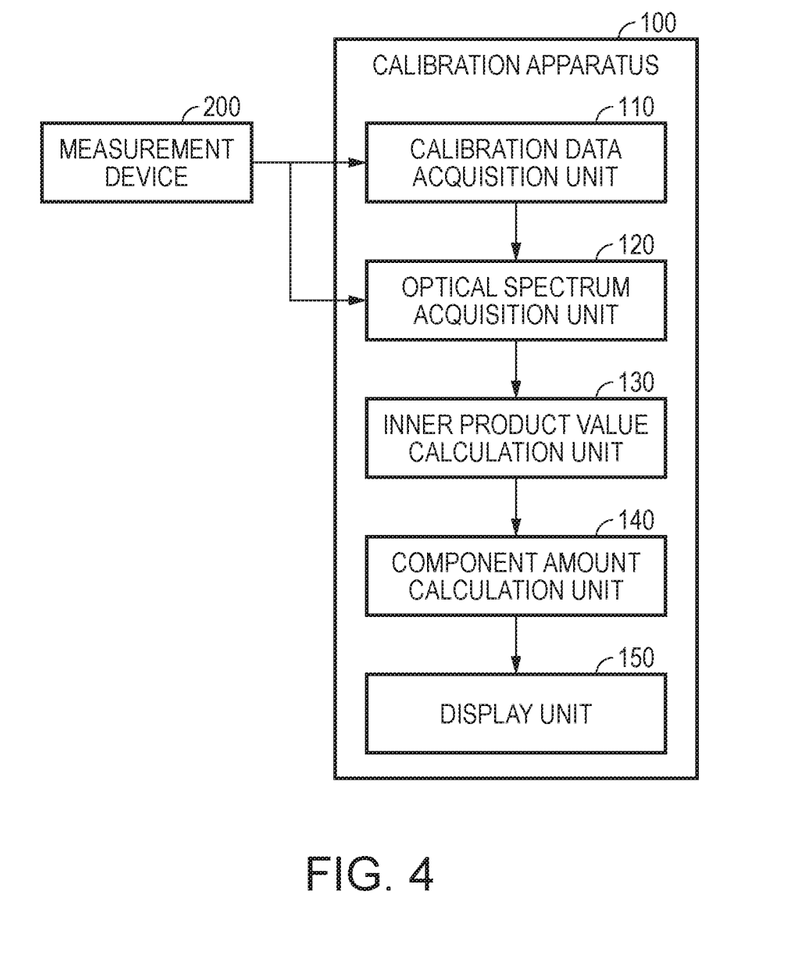
FIG. 4 is a block diagram illustrating a configuration of a calibration apparatus in an embodiment.

FIG. 4 is a block diagram illustrating a configuration of a calibration apparatus 100 in an embodiment. The calibration apparatus 100 includes a calibration data acquisition unit 110, an optical spectrum acquisition unit 120, an inner product value calculation unit 130, a component amount calculation unit 140, and a display unit 150. A measurement device 200 for acquiring measured data is connected to the calibration apparatus 100. The measurement device 200 is, for example, a spectrometer measuring spectral absorbance of a sample. The measurement device 200 is not limited to a spectrometer, and various measurement devices suitable for characteristics of target components can be used.

The calibration apparatus 100 may be implemented by, for example, an electronic apparatus for use in calibration only, and may be implemented by a general purpose computer. Functions of the respective units 110 to 150 of the calibration apparatus 100 may be implemented by any computer programs or hardware circuits.

Figure 5:
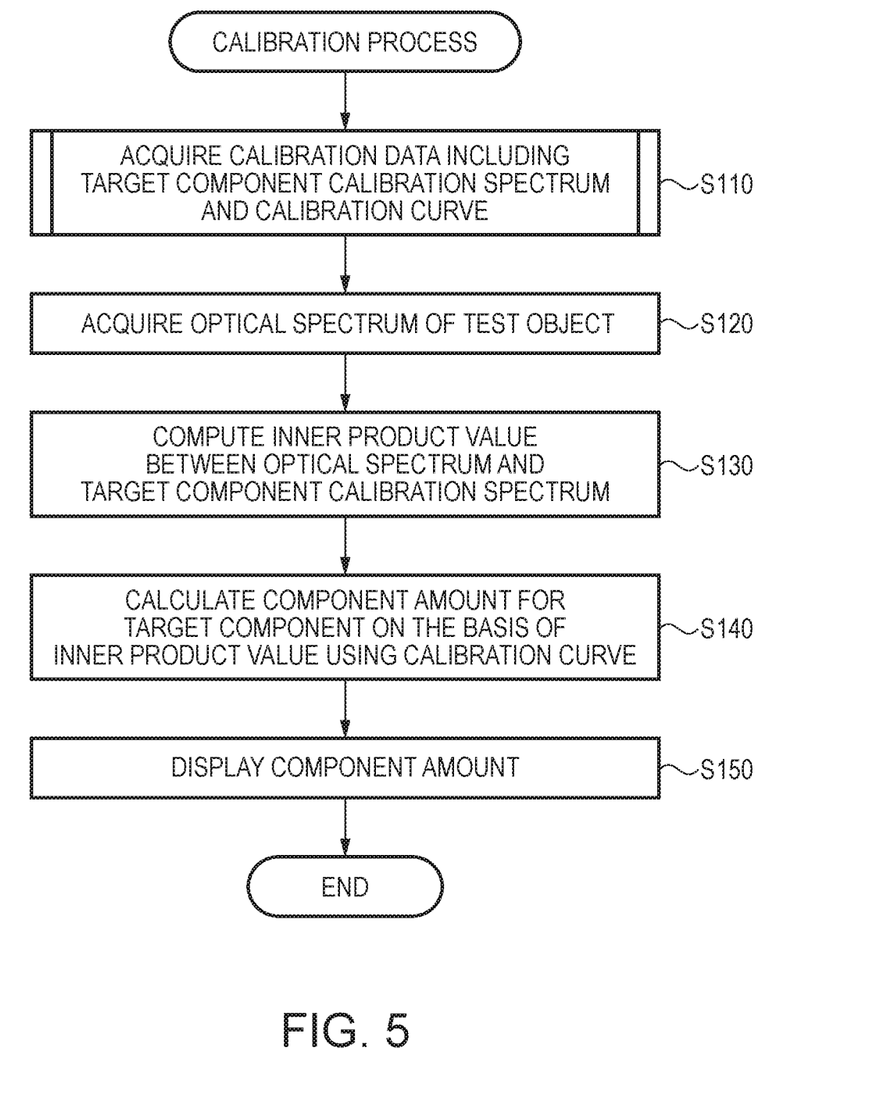
FIG. 5 is a flowchart illustrating procedures of a calibration process.

FIG. 5 is a flowchart illustrating procedures of a calibration process performed by the calibration apparatus 100. In step S110, the calibration data acquisition unit 110 (FIG. 4) acquires calibration data including a target component calibration spectrum ($CS_1$ in the example illustrated in FIG. 2) and the calibration curve CC. Details of the calibration data acquisition process in the present embodiment will be described later.

In step S120, the optical spectrum acquisition unit 120 acquires the optical spectrum. TOS (FIG. 3) of a test object by using the measurement device 200. As described in FIG. 3, the optical spectrum TOS is obtained by performing preprocessing on a measure spectrum obtained through spectrometry, as necessary. Therefore, the optical spectrum acquisition unit 120 preferably has a function of performing the preprocessing. In step S130, the inner product value calculation unit 130 calculates the inner product value P (FIG. 3) between the optical spectrum TOS and the target component calibration spectrum $CS_1$. In step S140, the component amount calculation unit 140 calculates the component amount C corresponding to the inner product value P obtained in step S130 by using the calibration curve CC. The component amount C is a component amount (for example, a glucose concentration) for the target component in the test object. In step S150, the component amount C is displayed on the display unit 150. Instead of the component amount C being displayed, the component amount C may be transmitted to another electronic apparatus, and other desired processes (for example, a notification sent to a test object using an electronic mail) may be performed.

D. CONTENT OF CALIBRATION DATA ACQUISITION PROCESS

Figure 6:
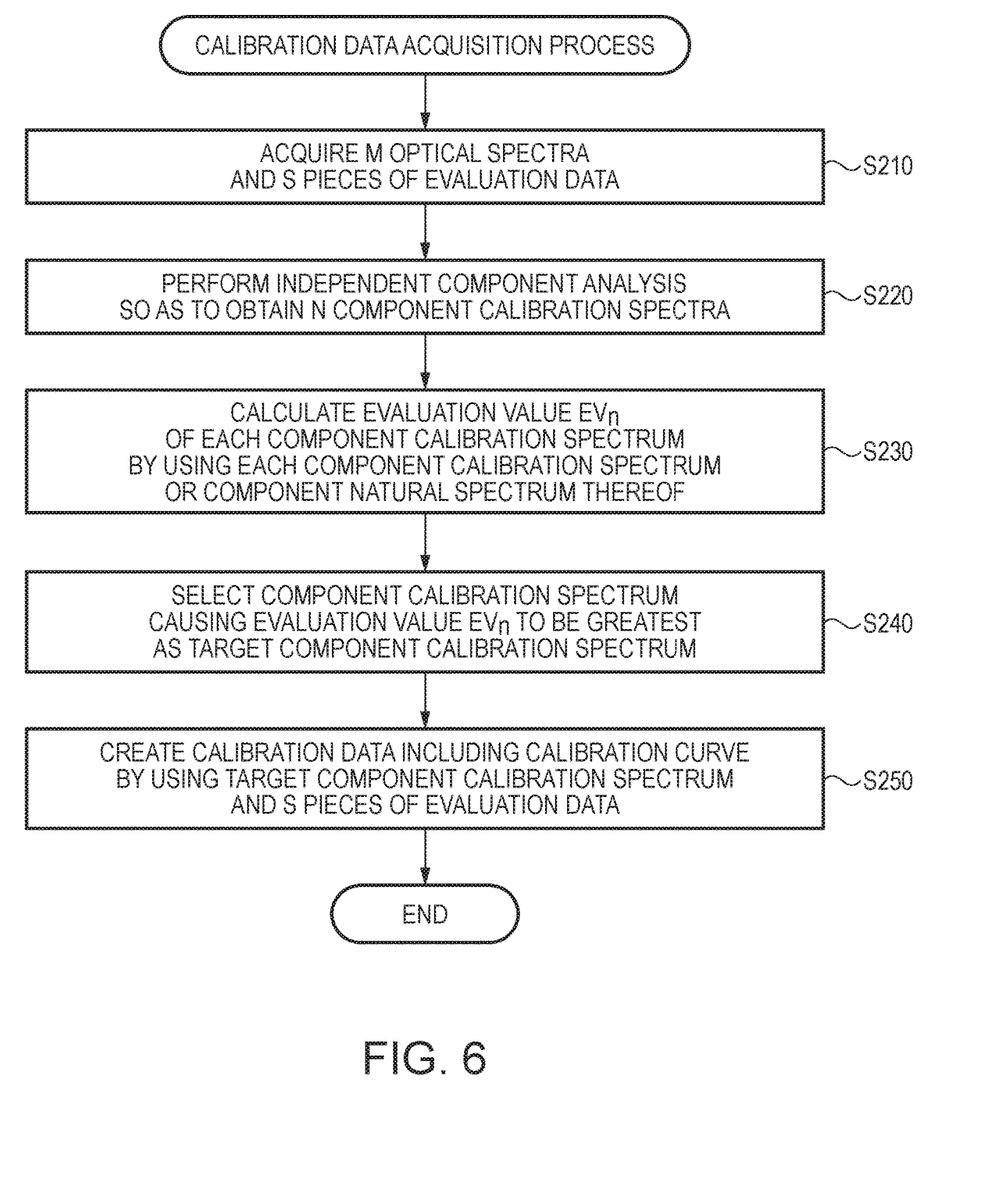
FIG. 6 is a flowchart illustrating a calibration data acquisition process.
Figure 7:
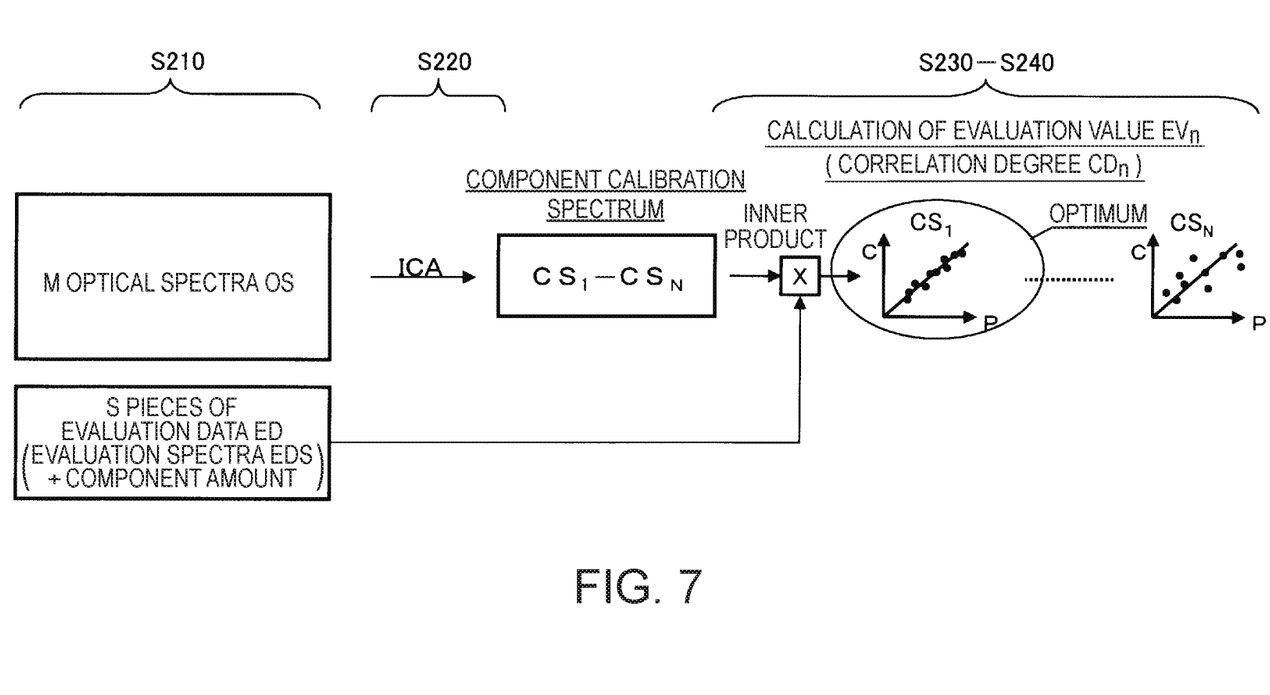
FIG. 7 is a diagram illustrating the content of the calibration data acquisition process.

FIGS. 6 and 7 are flowchart illustrating the calibration data acquisition process in the present embodiment and diagrams illustrating the content thereof, and illustrate detailed steps of step S110 in FIG. 5.

In step S210, measurement is performed on M (where M is an integer of 2 or more) first samples containing a plurality of components including a target component (for example, glucose) so that M optical spectra OS (FIG. 7) is acquired, and measurement is performed on S (where S is an integer of 3 or more) second samples in which a component amount for the target component is known so that S pieces of evaluation data ED (FIG. 7) are acquired. The M optical spectra OS are learning sample data for determining a component calibration spectrum by performing independent component analysis. The evaluation data ED includes the evaluation spectra EDS which are optical spectra for the S samples and a known component amount for the target component in each sample. In the M first samples, a component amount for the target component may be known, but samples in which a component amount for the target component is unknown may be used. This is because, in the calibration data acquisition process of the present embodiment, a component amount of the target component in the M first samples is not used.

The number S of second samples in which a component amount is known may be any integer of 3 or more, and a larger number S is preferable in that calibration accuracy is improved. Typically, the number S of second samples is smaller than the number M of first samples. Some or all of the second samples may be used as parts of the first samples.

In step S220, the independent component analysis in which a component amount is treated as an independent component is performed on the M optical spectra OS so that N (where N is an integer of 1 or more) component calibration spectra $CS_n$ (where n is 1 to N) are obtained (FIG. 7). The number N of components is not required to match the number of actually contained components, and is empirically or experimentally determined so that the accuracy of independent component analysis is improved. A value of N may be set to an integer of 1 or more, but may be an integer of 2 or more.

Steps S230 and S240 are processes of selecting an optimal target component calibration spectrum corresponding to the target component from among the N component calibration spectra $CS_n$ (where n is 1 to N) obtained in step S220. First, in step S230, an evaluation value $EV_n$ of each component calibration spectrum $CS_n$ is calculated by performing calculation using a function having, as a variable, each component calibration spectrum $CS_n$ $(=y_n^*)$ or a component natural spectrum $(y_n)$ corresponding thereto, with respect to each of the N component calibration spectra $CS_n$.

As the evaluation value $EV_n$, for example, a correlation degree indicating a correlation between the inner product value P and the component amount C described in FIG. 2 may be used. The inner product value P is obtained by computing an inner product between the S evaluation spectra EDS and each component calibration spectrum $CS_n$ as illustrated in FIG. 7. The component amount C is a known component amount C of the target component in the S second samples. FIG. 7 exemplifies a state in which the correlation degree $CD_n$ is calculated as the evaluation value $EV_n$ with respect to each component calibration spectrum $CS_n$. As the correlation degree $CD_n$, for example, a correlation coefficient may be used. In a case where the correlation degree $CD_1$ is used as the evaluation value $EV_n$, the following calculation formula using a function $f(CS_n)$ for inner product calculation is used to obtain the inner product value P.

$$P = f(CS_n) \qquad (8)$$
$$= CS_n(\lambda) \cdot EDS(\lambda)$$

The function $f(CS_n)$ is one kind of function having the component calibration spectrum $CS_n$ as a variable. In addition to the calculation formula in the above Equation (8), a calculation formula for obtaining the correlation degree $CD_n$ between the inner product value P and the component amount C is used for calculation of the correlation degree $CD_n$ as the evaluation value $EV_n$.

As the evaluation value $EV_n$, evaluation values other than the correlation degree $CD_n$ may be used. For example, a reference spectrum (standard spectrum) corresponding to a target component may be prepared in advance, and a similarity between the reference spectrum and each component natural spectrum $y_n$ may be used as the evaluation value $EV_n$. The similarity may be calculated according to various methods, and, for example, the following values may be used as the similarity.

(1) A correlation coefficient between the component natural spectrum $y_n$ and the reference spectrum RFS of the target component (2) An inner product between the component natural spectrum $y_n$ and the reference spectrum RFS of the target component (3) An inverse number of norm in a case where a difference between the component natural spectrum $y_n$ and the reference spectrum RFS of the target component is treated as multi-dimensional vector In order to obtain such a value, the component natural spectrum $y_n$ and the reference spectrum RFS of the target component are preferably normalized in advance.

As the evaluation value $EV_n$, a comprehensive evaluation value obtained by combining the above-described correlation degree $CD_n$ (or a similarity) and other index values with each other may be used. For example, in a case where the comprehensive evaluation value $EV_n$ obtained by combining the above-described correlation degree $CD_n$ and other index values with each other is used, it is preferable to calculate the evaluation value $EV_n$ by using a calculation formula in which the evaluation value $EV_n$ increases as the correlation degree $CD_n$ increases.

As can be seen from various examples of calculation of the evaluation value $EV_n$, in the present specification, "calculation using a function having each component calibration spectrum $CS_n$ (or each component natural spectrum $Y_n$) as a variable" is not limited to a case of directly calculating the evaluation value $EV_n$ by using the function once, and includes, in a broad sense, a case where the evaluation value $EV_n$ is calculated by performing further calculation on the basis of a computation result using the function.

In step S240, from among the N component calibration spectra $CS_1$ to $CS_N$, a single component calibration spectrum $CS_n$ causing the evaluation value $EV_n$ to be greatest is selected as a target component calibration spectrum corresponding to the target component. In the example illustrated in FIG. 7, since the correlation degree $CD_n$ is used as the evaluation value $EV_n$, and the correlation degree $CD_1$ of the component calibration spectrum $CS_1$ is highest, the component calibration spectrum $CS_1$ is selected as a target component calibration spectrum.

In step S250, the single regression formula C=uP+v (refer to FIG. 2) indicating a relationship between the S inner product values P obtained through an inner product between the S evaluation spectra EDS and the target component calibration spectrum $CS_1$, and the known component amount C for the target component in the S second samples is created as the calibration curve CC by using the target component calibration spectrum $CS_1$ selected in the above-described way. In a case where the correlation degree $CD_n$ is used as the evaluation value $EV_n$, the S inner product values P regarding the target component calibration spectrum $CS_1$ are already obtained in step S230, and thus the S inner product values P may be used without being changed in step S250.

As mentioned above, in the present embodiment, since independent component analysis in which component amounts for a plurality of components in each sample are treated as independent components is performed, the independent component analysis can be performed with high accuracy, and thus calibration of a target component can be performed with high accuracy, even in a case where optical spectra derived from a plurality of components are not independent from each other.

E. MODIFICATION EXAMPLES

The invention is not limited to the above-described embodiment or alternations thereof, and can be implemented in various aspects within the scope without departing from the spirit of the invention and may be modified as follows, for example.

Modification Example 1

In the above-described embodiment and Example, a description has been made of a case where an aqueous solution containing glucose is used as a sample, but the invention is applicable to other samples. For example, the invention is applicable to a case where a liquid containing a salt or liquid containing a protein such as a lipid or albumin or an alcohol is used as a sample. The invention is also applicable to independent component analysis in which other objects such as a human body (human), a voice, and an image are used as samples. In a case where a human body is an object, the invention is applicable to a case with neutral fat or alcohol in the human body, or glucose in blood as a target component. In a case where data or a signal other than a spectrum is an independent component analysis object, the word "spectrum" may be replaced with other words such as "measured data" or "object data".

Modification Example 2

Regarding apparatuses to which the invention is applicable, the invention is also applicable to an apparatus in which a component concentration is estimated on the basis of spectrometric data of an optically mid-infrared spectroscopic type, near-infrared spectroscopic type, or Raman spectroscopic type. The invention is also applicable to any one of an optical protein concentration meter, an optical neutral fat concentration meter, an optical blood glucose meter, an optical salt concentration meter, and an optical alcohol concentration meter.

The entire disclosure of Japanese Patent Application No. 2016-186729 filed Sep. 26, 2016 is hereby incorporated herein by reference.

What is claimed is:

1. A calibration apparatus which obtains a component amount for a target component in a test object, comprising:
   a non-transitory storage configured to store a program;
   a display configured to display the component amount for the target component in the test object; and
   a computer configured to execute the program so as to:
      acquire an optical spectrum obtained through spectrometry on the test object;
      acquire calibration data including a target component calibration spectrum corresponding to the target component, and a single regression formula indicating a calibration curve;
      compute an inner product value between the optical spectrum measured for the test object and the target component calibration spectrum; and
      calculate a component amount for the target component corresponding to the inner product value obtained by using the single regression formula indicating a relationship between the inner product value and the component amount for the target component,
   wherein the computer is further configured to perform:
      (a) a process of acquiring M optical spectra obtained through spectrometry on M (where M is an integer of 2 or more) first samples each containing N (where N is an integer of 1 or more) components including the target component, and S evaluation spectra obtained through the spectrometry on S (where S is an integer of 3 or more) second samples in which the component amount for the target component is known;
(b) a process of using an equation $X=YW$ in which an optical spectrum matrix $X$ having optical spectra obtained through the spectrometry on each of the M first samples as column vectors is the same as a product between a component natural spectrum matrix $Y$ having unknown component natural spectra derived from the N respective components as column vectors and a component amount matrix $W$ having unknown component amounts for the N components in each of the samples as column vectors, and performs independent component analysis in which the respective column vectors forming the component amount matrix $W$ are treated as independent components, so as to determine the component amount matrix $W$ and the component natural spectrum matrix $Y$, and also employs N row vectors of a general inverse matrix $Y^{\dagger}$ of the determined component natural spectrum matrix $Y$, as the N component calibration spectra corresponding to the N components;
(c) a process of performing calculation using a function having each component calibration spectrum or a component natural spectrum corresponding to the component calibration spectrum as a variable with respect to each of the N component calibration spectra, so as to calculate an evaluation value of each component calibration spectrum;
(d) a process of selecting a component calibration spectrum causing the evaluation value to be greatest as the target component calibration spectrum among the N component calibration spectra;
(e) a process of creating, as the calibration curve, the single regression formula indicating a relationship between the inner product value obtained through an inner product between the S evaluation spectra and the target component calibration spectrum and the component amount for the target component contained in the S second samples;
(f) a process of obtaining the component amount for the target component in the test object based on the single regression formula and the inner product value; and
(g) a process of displaying the component amount for the target component in the test object on the display.

2. A calibration curve creation method of creating a calibration curve used to obtain a component amount for a target component contained in a test object for causing a computer to execute a program stored in a non-transitory storage, the method comprising executing on the computer the steps of:
(a) acquiring M optical spectra obtained through spectrometry on M (where M is an integer of 2 or more) first samples each containing N (where N is an integer of 1 or more) components including the target component, and S evaluation spectra obtained through spectrometry on S (where S is an integer of 3 or more) second samples in which the component amount for the target component is known;
(b) using an equation $X=YW$ in which an optical spectrum matrix $X$ having optical spectra obtained through the spectrometry on each of the M first samples as column vectors is the same as a product between a component natural spectrum matrix $Y$ having unknown component natural spectra derived from the N respective components as column vectors and a component amount matrix $W$ having unknown component amounts for the N components in each of the samples as column vectors, and performs independent component analysis in which the respective column vectors forming the component amount matrix $W$ are treated as independent components, so as to determine the component amount matrix $W$ and the component natural spectrum matrix $Y$, and also employs N row vectors of a general inverse matrix $Y^{\dagger}$ of the determined component natural spectrum matrix $Y$, as the N component calibration spectra corresponding to the N components;
(c) performing calculation using a function having each component calibration spectrum or a component natural spectrum corresponding to the component calibration spectrum as a variable with respect to each of the N component calibration spectra, so as to calculate an evaluation value of each component calibration spectrum;
(d) selecting a component calibration spectrum causing the evaluation value to be greatest as the target component calibration spectrum among the N component calibration spectra;
(e) creating, as the calibration curve, a single regression formula indicating a relationship between an inner product value obtained through an inner product between the S evaluation spectra and the target component calibration spectrum and the component amount for the target component contained in the S second samples;
(f) obtaining the component amount for the target component in the test object based on the single regression formula and the inner product value; and
(g) displaying the component amount for the target component in the test object.

3. An independent component analysis method in which component calibration spectra corresponding to a plurality of components contained in each sample are determined on the basis of a plurality of optical spectra obtained through spectrometry on a plurality of samples, the method for causing a computer to execute a program stored in a non-transitory storage, the method comprising executing on the computer the steps of:
(1) using an equation $X=YW$ in which an optical spectrum matrix $X$ having optical spectra obtained through spectrometry on each of the plurality of samples as column vectors is the same as a product between a component natural spectrum matrix $Y$ having unknown component natural spectra derived from the plurality of respective components as column vectors and a component amount matrix $W$ having unknown component amounts for the plurality of components in each of the samples as column vectors, and performs independent component analysis in which the respective column vectors forming the component amount matrix $W$ are treated as independent components, so as to determine the component amount matrix $W$ and the component natural spectrum matrix $Y$;
(2) employing respective row vectors of a general inverse matrix $Y^{\dagger}$ of the component natural spectrum matrix $Y$ determined through the independent component analysis, as a plurality of component calibration spectra corresponding to the plurality of components;
(3) obtaining the component amount of the plurality of components contained in each sample based on an inner product value corresponding to an inner product between the plurality of optical spectra and the plurality of component calibration spectra; and (4) displaying the component amount of the plurality of components contained in each sample on a display.

\* \* \* \* \*